United States Patent
Willis (10) Patent No.: US 6,719,700 B1
(45) Date of Patent: Apr. 13, 2004

(54) ULTRASOUND RANGING FOR LOCALIZATION OF IMAGING TRANSDUCER

(75) Inventor: N. Parker Willis, Atherton, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/318,571

(22) Filed: Dec. 13, 2002

(51) Int. Cl.$^7$ ................................................ A61B 8/14
(52) U.S. Cl. ................................................ 600/462
(58) Field of Search .................... 600/437–472; 73/620–633; 367/7, 11, 130, 138; 128/916

(56) References Cited

U.S. PATENT DOCUMENTS

| | | |
|---|---|---|
| 5,000,185 A | 3/1991 | Yock |
| 5,054,492 A | 10/1991 | Scribner et al. |
| 5,389,848 A | 2/1995 | Trzaskos |
| 5,398,691 A | 3/1995 | Martin et al. |
| 5,412,619 A | 5/1995 | Bauer |
| 5,485,845 A | 1/1996 | Verdonk et al. |
| 5,596,990 A | 1/1997 | Yock et al. |
| 5,836,882 A | 11/1998 | Frazin |
| 5,938,602 A | 8/1999 | Lloyd |
| 5,954,649 A | 9/1999 | Chia et al. |
| 6,004,269 A | 12/1999 | Crowley et al. |
| 6,019,725 A | 2/2000 | Vesely et al. |
| 6,027,451 A | 2/2000 | McGee et al. |
| 6,248,075 B1 | 6/2001 | McGee et al. |
| 6,277,077 B1 | 8/2001 | Brisken et al. |
| 6,461,298 B1 | 10/2002 | Fenster et al. |
| 6,464,642 B1 | 10/2002 | Kawagishi |
| 6,490,474 B1 | 12/2002 | Willis et al. |

FOREIGN PATENT DOCUMENTS

WO WO 93/08757 5/1993

Primary Examiner—Ali M. Imam
(74) Attorney, Agent, or Firm—Bingham McCutchen LLP (57) ABSTRACT

The present invention provides systems and methods for localizing an ultrasound imaging transducer. The ultrasound imaging transducer is operated in a first resonant mode to transmit an ultrasound imaging signal. Image data is generated based on this transmitted ultrasound imaging signal. The ultrasound imaging transducer is also operated in a second resonant mode to transmit or receive an ultrasound positioning signal. The position of the imaging transducer can then be determined based on the transmitted or received ultrasound positioning signal.

33 Claims, 4 Drawing Sheets

RECEIVE

| | TXVR1 | TXVR2 | TXVR3 | TXVR4 | TXVR5 | TXVR6 | TXVR7 | TXVR8 | RX1 | RX2 | RX3 | RX4 | RX5 | IMAG/TX |
|---|---|---|---|---|---|---|---|---|---|---|---|---|---|---|
| TXVR1 | ✕ | d1 | d2 | d3 | d4 | d5 | d6 | d7 | d8 | d9 | d10 | d11 | d12 | d97 |
| TXVR2 | d13 | ✕ | d14 | d15 | d16 | d17 | d18 | d19 | d20 | d21 | d22 | d23 | d24 | d98 |
| TXVR3 | d25 | d26 | ✕ | d27 | d28 | d29 | d30 | d31 | d32 | d33 | d34 | d35 | d36 | d99 |
| TXVR4 | d37 | d38 | d39 | ✕ | d40 | d41 | d42 | d43 | d44 | d45 | d46 | d47 | d48 | d100 |
| TXVR5 | d49 | d50 | d51 | d52 | ✕ | d53 | d54 | d55 | d56 | d57 | d58 | d59 | d60 | d101 |
| TXVR6 | d61 | d62 | d63 | d64 | d65 | ✕ | d66 | d67 | d68 | d69 | d70 | d71 | d72 | d102 |
| TXVR7 | d73 | d74 | d75 | d76 | d77 | d78 | ✕ | d79 | d80 | d81 | d82 | d83 | d84 | d103 |
| TXVR8 | d85 | d86 | d87 | d88 | d89 | d90 | d91 | ✕ | d92 | d93 | d94 | d95 | d96 | d104 |
| IMAG/TX | d97 | d98 | d99 | d100 | d101 | d102 | d103 | d104 | d105 | d106 | d107 | d108 | d109 | ✕ |

TRANSMIT

ULTRASOUND RANGING FOR LOCALIZATION OF IMAGING TRANSDUCER

FIELD OF THE INVENTION

The present inventions generally relate to medical imaging devices and methods, and more particularly to systems and methods for ultrasonically imaging body tissue.

BACKGROUND OF THE INVENTION

For purposes of diagnosis and treatment planning, imaging techniques are commonly used in medical procedures to view the internal anatomy of a patient's body. In one imaging technique, an imaging catheter with a distally rotatable ultrasound transducer is inserted into the patient's body, e.g., through a blood vessel. Typically, the ultrasound transducer will be mounted on the distal end of a drive shaft that rotates within the catheter body. The drive shaft is typically composed of a counter wound spring coil to maximize the distal transfer and response of the rotational forces applied to the proximal end of the shaft, while maximizing lateral flexibility.

To obtain an interior image of the body tissue, the rotating ultrasound transducer transmits pulses of ultrasound energy into the body. A portion of the ultrasound energy is reflected off of the internal anatomy of the body back to the transducer. The reflected ultrasound energy (echo) impinging on the transducer produces an electrical signal, which is used to form a 360 degree cross-sectional interior image of the body. The rotating ultrasound transducer can be longitudinally translated, so that multiple cross-sectional images can be generated and later reconstructed into a three-dimensional interior image of the body tissue.

Oftentimes, it is desirable to localize the imaging catheter, so that it can be accurately guided within the target area of the patient's body. In addition, it is also desirable to localize the imaging plane of the rotating imaging transducer, so that the resultant ultrasound image can be properly displayed within the context of the target area based on the localized position of the ultrasound transducer. In one guidance system, a graphical representation of the imaging catheter is displayed in a three-dimensional computer-generated representation of a body tissue, e.g., a heart chamber. The three-dimensional representation of the body tissue is produced by mapping the geometry of the inner surface of the body tissue in a three-dimensional coordinate system. For example, a mapping device can be placed in contact with multiple points on the body tissue to obtain surface points, and a graphical surface can then be conformed to the mapped surface points. Alternatively, a mapping device can be moved around inside the body cavity to obtain interior points, and a graphical surface can be gradually deformed in real time to include each interior point as it is obtained. In this case, the mapping device can also be placed in contact with the body tissue to obtain surface points, so that the graphical deformation process can be further refined.

In any event, the position and orientation of the imaging catheter, and thus, the position and orientation of the imaging plane, are determined by placing one or more location sensors on the catheter body known distances from the imaging transducer, and then tracking the position of these sensor(s) within the three-dimensional coordinate system. The position and orientation of the imaging plane can be extrapolated from the determined positions and/or orientation of the sensor(s). In the case of an ultrasound-based guidance system, multiple location sensors (in the form of ultrasound transducers) are placed along the distal end of the imaging catheter, so that its angular orientation can be determined. An example of this type of guidance system is the Realtime Position Management™ (RPM) tracking system developed commercially by Cardiac Pathways Corporation, now part of Boston Scientific Corp. The RPM system is currently used in the treatment of cardiac arrhythmia to define cardiac anatomy, map cardiac electrical activity, and guide an ablation catheter to a treatment site in a patient's heart.

Although the use of these types of guidance systems are generally useful in tracking the position and orientation of an imaging catheter and its imaging plane, it is still desirable to make further improvements. For example, the addition of each location sensor incrementally increases the complexity and cost of the system, and thus, a reduction in the number of location sensors needed to localize the distal end of an imaging catheter would be beneficial. In addition, the overall length of the counterwound drive shaft will vary as the catheter body is curved, thereby shifting the position of the imaging transducer proximally or distally relative to the catheter body a distance up to 8 millimeters. This may cause inaccuracies when determining the position of the imaging transducer within the three-dimensional coordinate system. Also, the extrapolation process used to determine the position and orientation of the imaging plane may cause further inaccuracies.

There thus remains a need for an improved system and method for localizing an imaging ultrasound transducer.

SUMMARY OF THE INVENTION

In accordance with a first aspect of the present inventions, a method of localizing an. ultrasound imaging transducer is provided. The method comprises operating the ultrasound imaging transducer in a first resonant mode to transmit an ultrasound imaging signal (e.g., a 9 MHz ultrasound pulse) and generating image data based on the transmitted imaging signal. For example, the image data generation can comprise processing a portion of the transmitted imaging signal that reflects off an object. The image data can represent any desired subject to be imaged, but in one preferred method, the imaging signal is transmitted into the body of a patient, in which case, the image data can be tissue image data. If the body of a patient is to be imaged, the imaging transducer is preferably introduced within the body of the patient. The imaging transducer can be located outside of the patient's body, however, to externally obtain image data.

The method further comprises operating the imaging transducer in a second resonant mode to either transmit, receive, or transmit and receive, an ultrasound positioning signal (e.g., a 1 MHz ultrasound pulse), and determining a position of the imaging transducer based on the transmitted or received positioning signal, e.g., within a three-dimensional coordinate system. For example, the imaging transducer position determination can comprise calculating a distance between the imaging transducer and one or more ultrasound reference transducers by calculating a time period defined by the time of flight of the position signal between the imaging transducer and reference transducer(s). The imaging transducer can optionally be rotated around an axis so that the image data comprises 360° cross-sectional image data. Although the present inventions should not be so limited in their broadest aspects, it can be appreciated that the operation of the imaging transducer in multiple modes allows the imaging transducer to be more accurately localized with or without the use of additional tracking transducers.

In one preferred method, the imaging transducer is conveniently operated in the first and second resonant modes by stimulating the imaging transducer with a single electrical signal. The imaging transducer can be operated in the two modes, however, by stimulating the imaging transducer with separate signals as well. In another preferred method, the imaging transducer exhibits a first isotropy radio when operated in the first resonant mode, and a second isotropy ratio greater than the first isotropy ratio, e.g., less than 10, when operated in the second resonant mode. In this manner, the positioning signal can be effectively received by any location surrounding the imaging transducer, and the imaging signal, itself, will be more focused.

In accordance with a second aspect of the present inventions, an ultrasound imaging transducer localization system is provided. The localization system comprises an ultrasound imaging transducer having first and second resonant modes, and control/processing circuitry coupled to the ultrasound transducer for operating the imaging transducer in the first resonant mode to transmit an ultrasound imaging signal (e.g., a 9 MHz ultrasound pulse), and for operating the imaging transducer in the second resonant mode to transmit or receive an ultrasound positioning signal (e.g., a 1 MHz ultrasound pulse). The control/processing circuitry is configured for generating image data based on the transmitted ultrasound imaging signal, and for determining a position of the imaging transducer based on the transmitted or received ultrasound positioning signal. The control/processing circuitry implemented in hardware, software, firmware, or any combination thereof.

In one preferred embodiment, the localization system further comprises a probe, such as, e.g., a catheter, on which the imaging transducer is mounted. In the preferred embodiment, the imaging transducer can be rotatable, in which case, the localization system can further comprise a drive unit a drive unit mechanically coupled to the imaging transducer for rotating the imaging transducer around an axis. In this manner, the control/processing circuitry can generate 360° cross-sectional image data. The imaging transducer can, however, be non-rotatable. The control/processing circuitry can operate the imaging transducer in the first and second resonant modes, generate the imaging data, and determine the position of the imaging transducer in the same manner described above. The imaging transducer can exhibit the same characteristics as those previously described.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
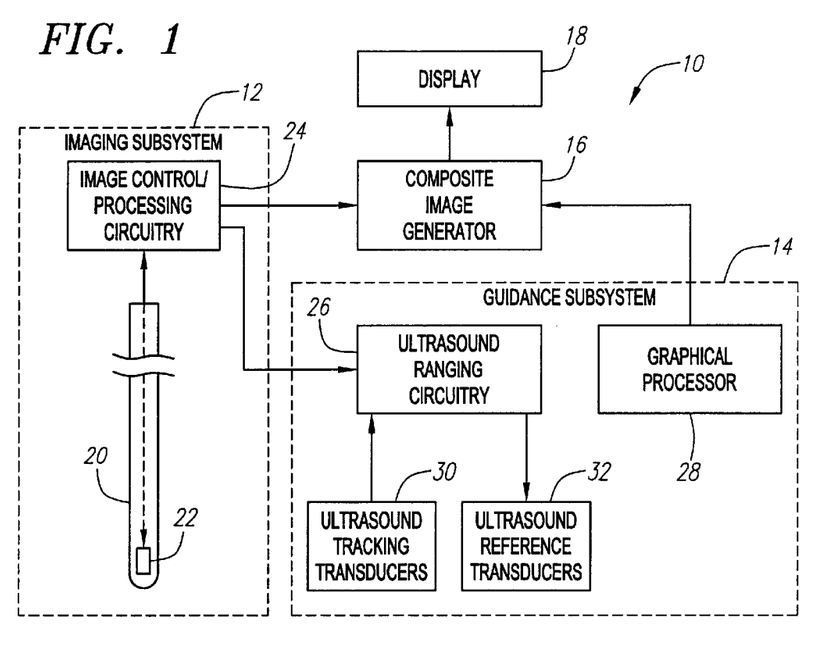
FIG. 1 is a functional block diagram of one preferred embodiment of a body tissue imaging system constructed in accordance with the present inventions.

Referring to FIG. 1, an exemplary body tissue imaging system 10 constructed in accordance with the present inventions is shown. The imaging system 10 generally comprises (1) an imaging subsystem 12 for generating image data of body tissue, e.g., a heart; (2) a guidance subsystem 14 for localizing the image data within a three-dimensional graphical environment; (3) a composite image generator 16 for generating a composite image by registering the image data with the three-dimensional graphical environment; and (4) a display 18 for displaying the composite image. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

The imaging subsystem 12 comprises an ultrasound imaging catheter 20, which includes a distally rotatable ultrasound imaging transducer 22 for generating and detecting imaging signals representing the interior of the body, and ultrasound imaging control/processing circuitry 24 coupled to the imaging catheter 20 for processing these signals into image data.

Figure 2:
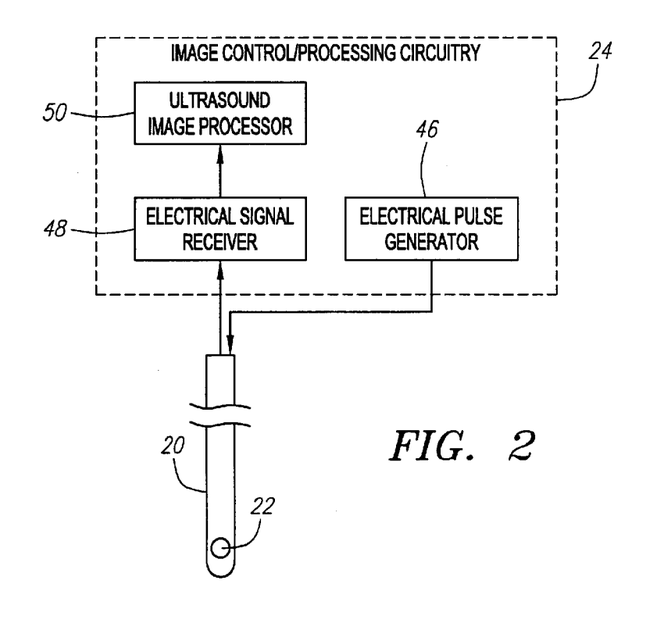
FIG. 2 is a functional block diagram of an ultrasound imaging subsystem used in the body tissue imaging system of FIG. 1.
Figure 3:
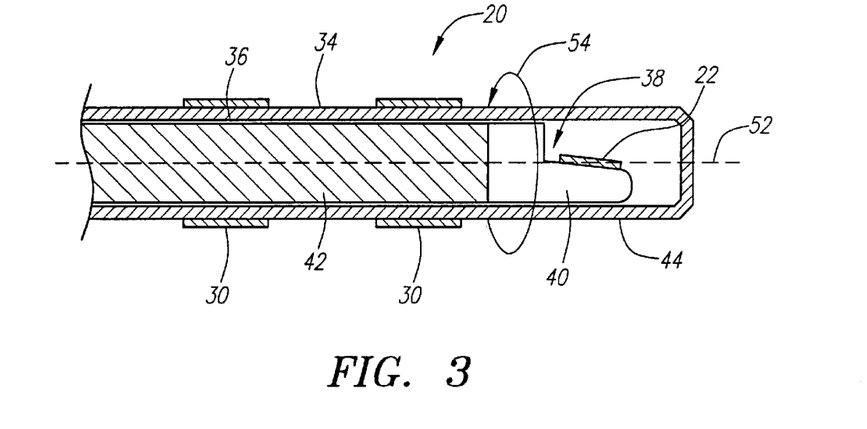
FIG. 3 is a cross-sectional view of an ultrasonic imaging catheter used in the ultrasound imaging subsystem of FIG. 2.

Specifically, and with reference to FIGS. 2 and 3, the ultrasound imaging catheter 20 comprises an elongated catheter body or sheath 34 having a lumen 36 extending therethrough. The catheter body 34 is made of a flexible material, so that it is able to be easily introduced through a body lumen, such as, e.g., an esophagus or a blood vessel. The imaging catheter 20 further comprises a rotatable imaging assembly 38, which comprises a housing 40 (or "can") and the imaging transducer 22. The imaging catheter 20 further comprises a drive shaft 42 extending through the lumen 36. The rotating imaging assembly 38 is mounted on the distal end of the drive shaft 42, and a drive motor (not shown) is mounted to the proximal end of the drive shaft 42. The catheter body 34 includes an acoustic window 44 for allowing ultrasound pulses to pass through the catheter body 34. The lumen 36 may be filled with fluid, e.g., water, to better couple ultrasound energy from the imaging transducer 22 to the surrounding body.

The imaging control/processing circuitry 24 includes an electrical pulse generator 46 and an electrical signal receiver 48, both of which are coupled to the imaging transducer 22 via signal wires (not shown) that extend through the center of the drive shaft 42. The imaging control/processing circuitry 24 further includes an ultrasound image processor 50 coupled to the electrical signal receiver 48.

To obtain an ultrasound image of the interior of the body, the imaging catheter 20 may be inserted into the body with the imaging transducer 22 adjacent the tissue to be imaged, and the imaging assembly 38 is operated to generate an imaging beam that rotates about an axis 52 and forms a rotational plane 54. Specifically, the imaging assembly 38 is mechanically rotated along the axis 52, while the pulse generator 46 transmits electrical pulses through the signal wires to excite the imaging transducer 22. In the illustrated embodiment, the imaging assembly 38 is rotated at 30 revolutions/second, and the pulse generator 46 generates 9 MHz pulses at a rate of 256 pulses per revolution. The imaging transducer 22 converts the electrical pulses into pulses of ultrasound energy, which are emitted into the body tissue. A portion of the ultrasound energy is reflected off of the body tissue back to the imaging transducer 22. The imaging transducer 22 converts the back-reflected ultrasound energy into electrical signals representing the body tissue, which are transmitted back through the signal wires to the electrical signal receiver 48. The electrical signals are detected by the electrical signal receiver 48 and outputted to the ultrasound image processor 50, which processes the received electrical signals into 360 degree cross-sectional ultrasound image data of the body tissue using known ultrasound image processing techniques. For each cross-section of image data, the ultrasound image processor 50 selects a fiducial orientation (in the illustrated embodiment, that associated with the generation of the first pulse) that will be used to orient the imaging data. Proper rotational orientation of the imaging data can be achieved using any one of a variety of imaging orientation methods, such as those described in U.S. Pat. No. 6,248,075, entitled "Method and Apparatus for Fixing the Anatomical Orientation of a Displayed Ultrasound Generated Image," and copending U.S. patent. application Ser. No. 10/319,285, entitled "Method and Apparatus for Reorienting a Medical Image," both of which are fully and expressly incorporated herein by reference.

To image a three-dimensional volume of the body, the imaging assembly 38 may be translated axially within the catheter body 34 by pulling back the drive shaft 42 with the drive motor. As the imaging assembly 38 is axially translated, the imaging transducer 22 is rotated to obtain multiple cross-sectional images (i.e., "slices") of the body tissue at different positions within the body. In this case, the ultrasound image processor 50 then aggregates (i.e., pieces together) the multiple cross-sectional images to reconstruct the volume of the body using known volume reconstruction techniques.

Referring back to FIG. 1, the guidance subsystem 14 generally comprises ultrasound ranging circuitry 26 for determining the distances between ultrasound tracking transducers 30, the imaging transducer 22 (which also functions as a tracking transducer), and ultrasound reference transducers 32. As will be described further detail below, the distances between the reference transducers 32 can be triangulated to establish a three-dimensional coordinate system, and the distances between the tracking transducers 30 and the reference transducers 32 can be triangulated to determine the positions (x,y,z) of the tracking transducers 30, and thus any structure or tissue adjacent the tracking transducers 30, within the established coordinate system. Similarly, the distances between the imaging transducer 22 and the reference transducers 32 can be triangulated to determine the positions (x,y,z) of the imaging transducer 22, and thus the rotational plane, within the established coordinate system.

In the illustrated embodiment, the ultrasound reference transducers 32 are mounted on a pair of reference catheters (not shown). For example, the number of reference transducers 32 can total eight, with four reference transducers 32 mounted on each reference catheter. The reference catheters can be placed anywhere within the body (preferably, a known location) that arranges the reference transducers 32 in three-dimensional space, and that allows the reference transducers 32 to communicate with the tracking transducers 30 and imaging transducer 22. For example, if the body tissue to be imaged is heart tissue, the first two dimensions of the coordinate system are provided by placing one of the reference catheters within the coronary sinus (CS) to arrange its four reference transducers 32 in a two-dimensional plane, and the third dimension is provided by placing by placing the other reference catheter within the right venticular (RV) apex to arrange its four reference transducers 32 off of the two-dimensional plane. It should be noted that only three of the reference transducers 32 located on the CS reference catheter are needed to provide the first two dimensions of the coordinate system, while only one of the reference transducers 32 located on the RF reference catheter is needed to provide the third dimension. The remaining reference transducers 32 are redundant and are used to improve the accuracy of the triangulation process.

In the illustrated embodiment, two cylindrically-shaped tracking transducers 30 are mounted about the distal end of the imaging catheter body 34 (shown in FIG. 3). If the body tissue to be analyzed is a heart chamber, tracking transducers 30 can also be mounted at the distal end of a mapping catheter (not shown) to facilitate the mapping of electrophysiological information within the heart chamber. One of the tracking transducers 30 can be mounted on the distal tip of the mapping catheter, or alternatively, this tracking transducer 30 can be mounted on the distal tip of a separate marking catheter (not shown), so that the inner surface of the heart chamber can be structurally mapped.

In the illustrated embodiment, the reference transducers 32 are operated as transceivers (i.e., they have the capability of transmitting and receiving ultrasound pulses), the tracking transducers 30 are operated as receivers, and the imaging transducer 22 is operated as a transmitter. As will be described in further detail below, operating the imaging transducer 22 as a transmitter provides certain design advantages. It should be noted, however, that the imaging transducer 22, like the reference transducers 32 and tracking transducers 30, can be operated as a transceiver or receiver without straying from the principles taught by this invention.

The reference transducers 32 are operated as transmitters by stimulating them with electrical pulses, which in turn causes the reference transducers to vibrate and transmit ultrasound pulses. The reference transducers 32 and tracking transducers 30 are operated as receivers by stimulating them with ultrasound pulses, which in turn causes the reference transducers to vibrate and transmit electrical pulses.

The ultrasound transducers are composed of piezoelectric ceramics that convert electrical energy into vibrational energy, and vice versa. This vibration results from the piezoelectric ceramic expanding in one direction, which causes it to contract in another direction. The expansion and contraction causes an ultrasound signal or pulse to be emitted from each surface of the transducer when transmitting. Similarly, a received ultrasound signal or pulse causes a receiving transducer to expand and contract, generating electricity. Each direction of expansion/contraction is termed a vibrational mode. Each vibration mode of a transducer is associated with a resonant frequency (i.e., the frequency of expansion/contraction), which is determined by the size and geometry of the transducer, and the speed of sound, s, in the piezoelectric ceramic, which is known to be approximately 4000 m/sec.

Figures 4, 5, 6:
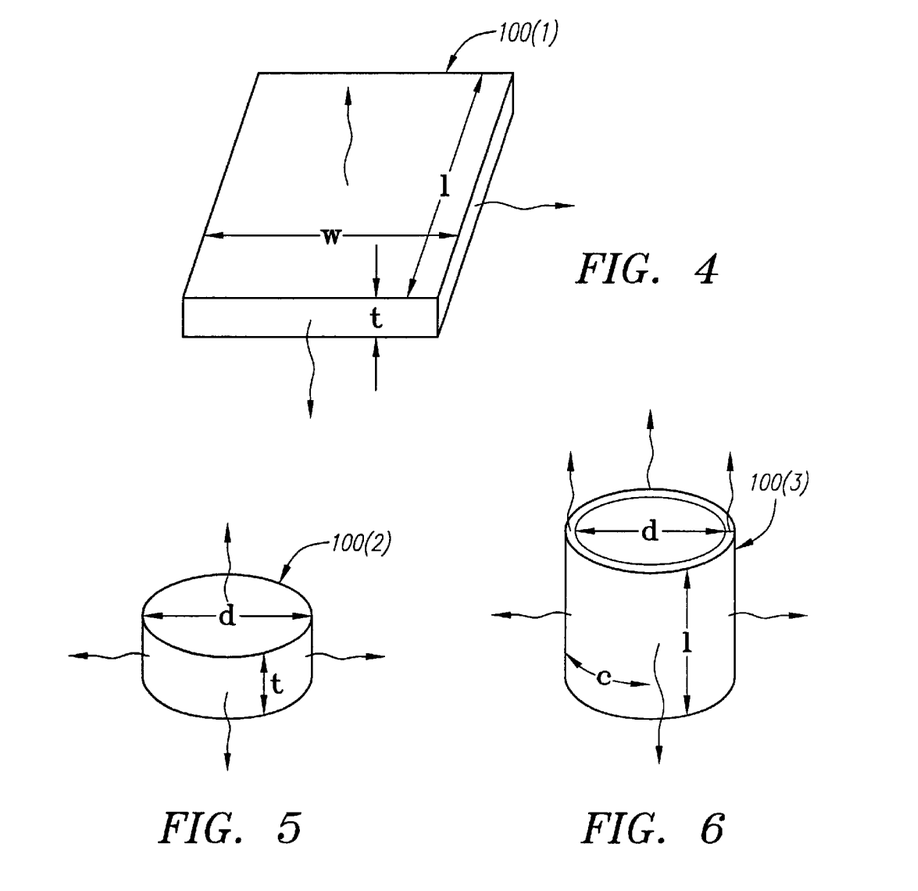
FIG. 4 is a perspective view of a square ultrasound transducer, particularly illustrating its resonant modes.
FIG. 5 is a perspective view of a disk-shaped ultrasound transducer, particularly illustrating its resonant modes.
FIG. 6 is a perspective view of a cylindrical ultrasound transducer, particularly illustrating its resonant modes.

For example, FIGS. 4–6 illustrate ultrasound transducers 100 with varying geometries. In FIG. 4, a square transducer 100(1) exhibits two resonant modes: (1) a thickness mode, which is caused by expansion/contraction along the thickness t of the transducer 100(1) and results in ultrasound energy being emitted from its face; and (2) a planar mode, which is caused by expansion/contraction along the plane p of the transducer 100(1) and results in ultrasound energy being emitted from its edges. The resonant frequency, f, of the transducer 100(1) when operated in the thickness mode can be given by $f=s/2t$. Assuming that the transducer 100(1) has a thickness, t, of 0.0087 inches, it will exhibit a resonant frequency, f, of 9 MHz when operated in the thickness mode. The resonant frequency, f, of the transducer 100(1) when operated in the planar mode can be given by $f=s/2l$. Assuming that the transducer 100(1) has a length, l, of 0.079 inches, it will exhibit a resonant frequency, f, of 1 MHz when operated in the planar mode.

In FIG. 5, a disk-shaped transducer 100(2) exhibits two resonant modes: (1) a thickness mode, which is caused by expansion/contraction along the thickness t of the transducer 100(2) and results in ultrasound energy being emitted from its face; and (2) a radial mode, which is caused by expansion/contraction along the diameter d of the transducer 100(2) and results in ultrasound energy being radially emitted from its circumference. The resonant frequency, f, of the transducer 100(2) when operated in the thickness mode can be given by $f=s/2t$. Assuming that the transducer 100(2) has a thickness, t, of 0.0087 inches, it will exhibit a resonant frequency, f, of 9 MHz when operated in the thickness mode. The resonant frequency, f, of the transducer 100(2) when operated in the radial mode can be given by $f=s/2d$. Assuming that the transducer 100(2) has a diameter, d, of 0.079 inches, it will exhibit a resonant frequency, f, of 1 MHz when operated in the radial mode.

In FIG. 7, a cylindrical transducer 100(3) exhibits two resonant modes: (1) a length mode, which is caused by expansion/contraction along the length l of the transducer 100(3) and results in ultrasound energy being emitted from its edges; and (2) a circumferential mode, which is caused by expansion/contraction along the circumference c of the transducer 100(3) and results in ultrasound energy being radially emitted from its circumference c. The resonant frequency, f, of the transducer 100(3) when operated in the length mode can be given by $f=s/2l$. Assuming that the transducer 100(3) has a length, l, of 0.0087 inches, it will exhibit a resonant frequency, f, of 9 MHz when operated in the length mode. The resonant frequency, f, of the transducer 100(3) when operated in the circumferential mode can be given by $f=s/\pi d$. Assuming that the transducer 100(2) has a diameter, d, of 0.050 inches, it will exhibit a resonant frequency, f, of 1 MHz when operated in the circumferential mode.

It is this multi-vibrational mode phenomenon that allows the imaging transducer 22 to provide a positioning function in addition to the imaging function. That is, the imaging transducer 22 is advantageously operated in two resonant modes (thickness and radial), such that it transmits imaging ultrasound pulses in the thickness mode (at 9 MHz) and transmits positioning ultrasound pulses in the radial mode (at 1 MHz). In this case, the imaging transducer 22 is shaped as a disk having a thickness, t, of 0.0087 inches, and a diameter, d, of 0.079 inches. The reference transducers 32 and tracking transducers 30 are capable of receiving the ultrasound pulses that are transmitted from the imaging transducer 22 in the radial mode. Thus, it can be appreciated that the use of the imaging transducer 22 to perform positioning, eliminates the need for an additional tracking transducer 30. It can also be appreciated that operating the imaging transducer 22 as a transmitter during the positioning function requires minimal or no modification to existing imaging equipment, since, during the imaging function, the imaging transducer 22 inherently transmits ultrasound pulses that could be used for positioning. No amplifiers or filters need be incorporated into existing the imaging device, which may otherwise be required if the imaging transducer 22 is operated as a receiver or transceiver.

Notably, the electrical pulse transmitted to the imaging transducer 22 is relatively short in order to increase the imaging resolution of resulting image data. Although this electrical pulse is nominally 9 MHz, its relatively short width spreads the harmonic frequencies over a broad range, which includes 1 MHz. Thus, the 9 MHz electrical pulse will stimulate the thickness and radial modes of the imaging transducer 22, so that it transmits 9 MHz and 1 MHz ultrasound pulses.

Ideally, the beam profile of the ultrasound pulses transmitted and/or received by the tracking transducers 30, imaging transducer 22 (in the radial mode), and reference transducers 32 is isotropic. That is, each of the ultrasound pulses has a beam profile that is substantially equal in all directions. In contrast, a beam profile that is anisotropic exhibits low points or nulls that may cause inconsistent measurements between transducers. Because the discontinuities between the different surfaces of the ultrasound transducer create discontinuities in its beam profile, however, ultrasound transducers, such as those illustrated in FIGS. 4–6, tend to be anisotropic to a certain extent. For example, in the illustrated embodiment, the ultrasound pulses transmitted and received by the tracking and reference transducers 30 and 32 exhibit an isotropic ratio (ratio of largest to smallest amplitude of beam profile) of approximately 3. The ultrasound pulses transmitted by the imaging transducer 22 when operated in the radial mode is 6. Typically, however, these isotropic ratios are sufficient to perform accurate distance measurements between the transducers.

To determine the distances between the tracking and reference transducers 30 and 32, the ranging circuitry 26 is operated to cause each reference transducer 32 to transmit an ultrasound pulse to the remaining reference transducers 32 and the tracking transducers 30, and then calculate the "time-of-flight" of each ultrasound pulse. The ranging circuitry 26 is also operated to calculate the time-of-flight of the ultrasound pulses transmitted by the imaging transducer 22 during its positioning function to the tracking and reference transducer 30 and 32.

Figure 7:
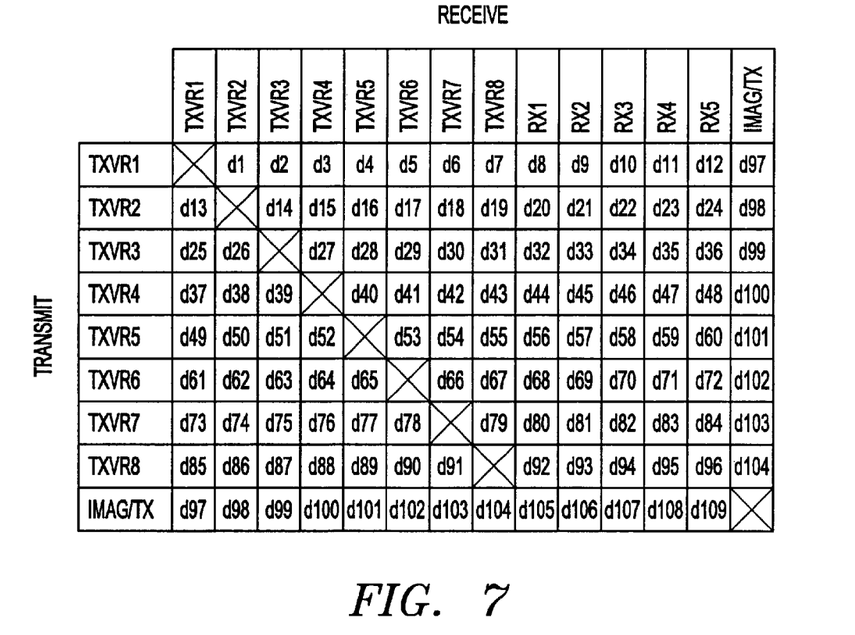
FIG. 7 is a table illustrating a distance matrix formed by calculating the distances between ultrasound tracking transducers, an ultrasound imaging transducer, and ultrasound reference transducers of an ultrasound ranging system.

Thus, it can be seen from FIG. 7 that a nine-by-thirteen distance matrix, defined by the nine transmitting transducers on one side (eight reference transducers 32 (TXVR1-8) and one imaging transducer 22 (IMAG/TX) and thirteen receiving transducers on the other side (eight reference transducers 32 (TXVR1-8), two tracking transducers 30 (RX1-2) located on the imaging catheter 20, and three tracking transducers 30 (RX3-5) located on the mapping catheter), is formed. This matrix contains the time-of-flight of the ultrasound pulses transmitted between each transmitting transducer and the respective receiving transducers. The distances (d1–d109) between the respective transducers can then be calculated using these time-of-flight values.

Figure 8:
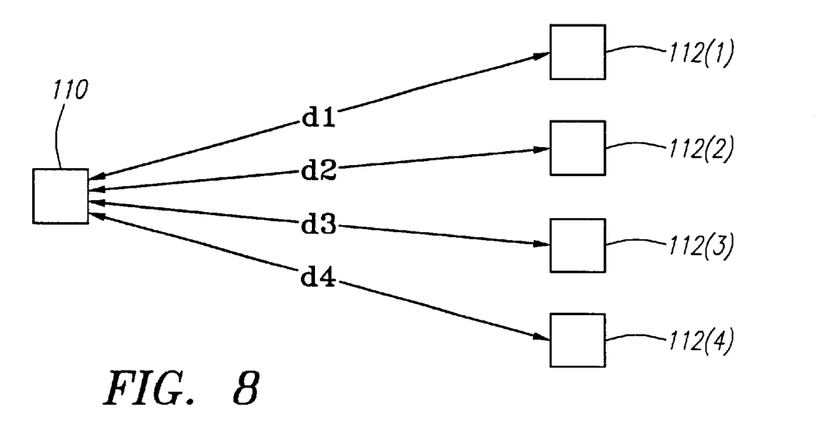
FIG. 8 is a functional block diagram of a positional arrangement between a plurality of ultrasound receiving transducers and an ultrasound transmitting transducer.

For example, referring to FIG. 8, a transmitting transducer 110 and four receiving transducers 112(1)–(4) are shown being separated from each other by respective distances d1–d4. To measure the distances d1–d4 between the transmitting transducer 110 and the receiving transducers 112, the equation $d=v\tau$ can be used, where $v$ is the velocity of the ultrasound pulse transmitted by the transmitting transducer 110 through the medium to the receiving transducers 112, and $\tau$ is the time that it takes for the ultrasound pulse to travel between the transmitting transducer and the respective receiving transducer 112. To simplify the distance computations, the velocity of the ultrasound pulses may be assumed to be constant. This assumption typically only produces a small error since the velocity of ultrasound pulses varies little in body tissue and blood.

Figure 9:
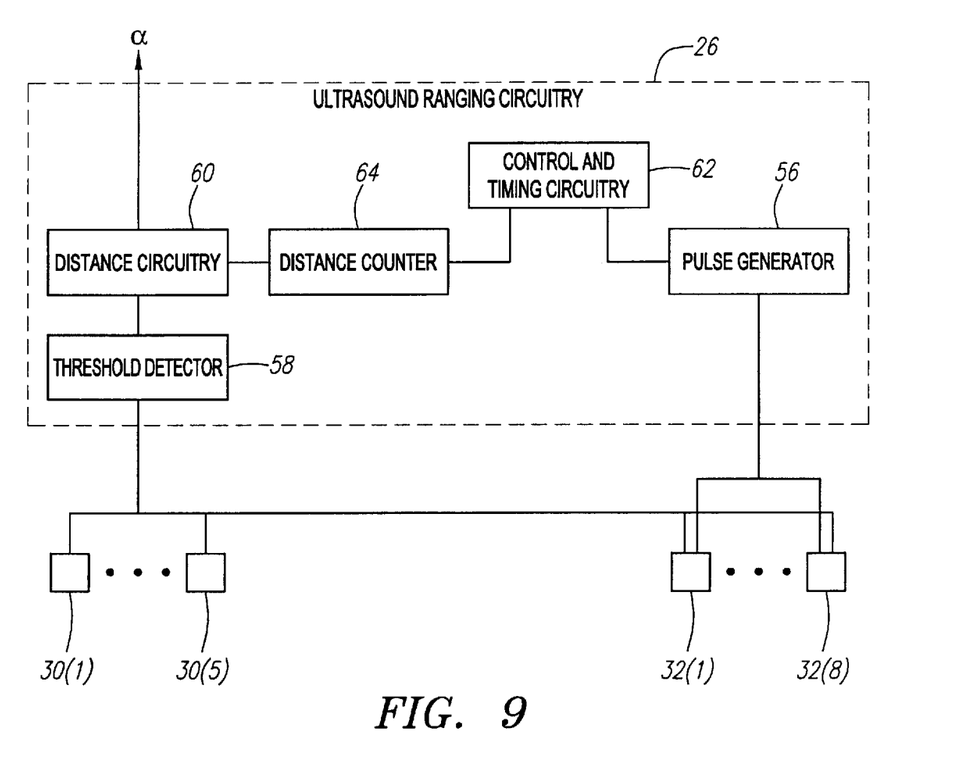
FIG. 9 is a functional block diagram of ultrasound ranging circuitry used in the body tissue imaging system of FIG. 1.

Turning now to FIG. 9, the components of the ranging circuitry 26 will now be described in further detail. The ranging circuitry 26 includes a pulse generator 56 coupled to the reference transducers 32, a threshold detector 58 coupled to the reference transducers 32 and the tracking transducers 30, distance circuitry 60 coupled to the threshold detector 58, control circuitry 62 coupled to the pulse generator 46, and a distance counter 64 coupled to the control circuitry 62.

Figure 10:
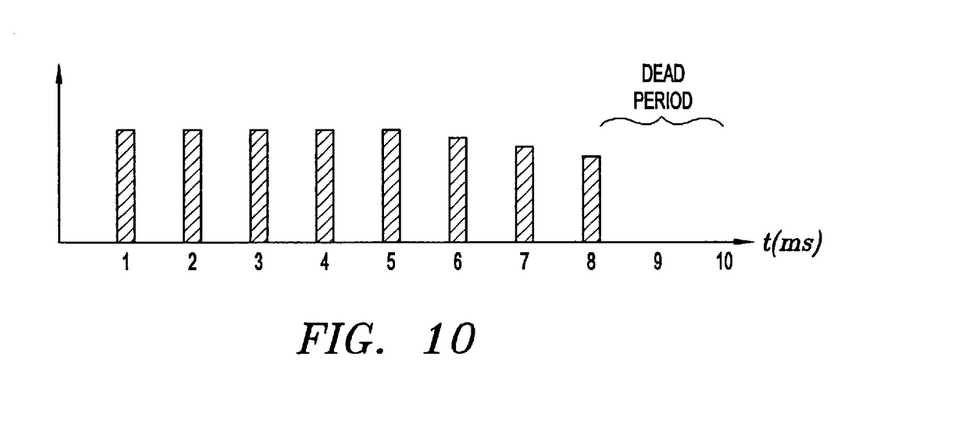
FIG. 10 is a diagram showing an exemplary series of ultrasound pulses transmitted by the ultrasound ranging circuitry of FIG. 9.

The pulse generator 46 is configured for generating electrical pulses that are transmitted to the reference transducers 32, which convert the electrical pulses into ultrasound pulses. The control circuitry 62 operates the pulse generator 46, such that the pulses are generated at the desired frequency and spacing. In the illustrated embodiment, the electrical pulses are 1 MHz pulses that are transmitted at a rate of one pulse per millisecond. Notably, the 1 MHz ultrasound pulses transmitted by the reference transducers 32 are consistent with the 1 MHz ultrasound pulses generated by the imaging transducer 22 in the radial mode. The control circuitry 62 also controls the multiplexing between the pulse generator 46 and the reference transducers 32, such that reference transducers 32 are stimulated by the electrical pulses in a sequential fashion. Thus, the control circuitry 62 will cause the first reference transducer 32(1) to transmit an ultrasound pulse, then the second reference transducer 32(2), and so on until the last reference transducer 32(8) transmits an ultrasound pulse. The control circuitry 62 will then cycle through the reference transducers 32 again. As illustrated in FIG. 10, a dead period is created at the end of each cycle in order to provide a separate transmission period for the imaging transducer 22, as will be described in further detail below. In the illustrated embodiment, this dead period extends for 1 millisecond. Thus, each transmission cycle is 9 milliseconds.

Coincident with the transmission of each ultrasound pulse from a reference transducer 32, the control circuitry 62 is configured for triggering the distance counter 64 to begin counting from zero. The running count value of the distance counter 64 provides a measure of time from the transmission of the ultrasound pulse. This distance counter 64 is reset to zero upon the transmission of the next ultrasound pulse. The control circuitry 62 is coupled to the image control/processing circuitry 24, so that it can determine when the ultrasound pulse has been transmitted from the imaging transducer 22. In the illustrated embodiment, the image control/processing circuitry 24 transmits a trigger pulse to the control circuitry 62 to indicate transmission of a ultrasound pulse from the imaging transducer 22.

After each ultrasound pulse has been transmitted, the remaining transducers receive the ultrasound pulse and convert the ultrasound pulse into respective electrical pulses. The threshold detector 58 is configured for detecting the electrical pulses that are above a threshold level, e.g., a voltage level. Upon receipt of a detected electrical pulse from the threshold detector 58, the distance circuitry 60 reads the current count from the distance counter 64, which provides a distance measurement between the corresponding receiving transducer and the current transmitting transducer in the form of an elapsed time between the transmission of the transmit pulse and the detection of the receive pulse. The distance circuitry 60 listens for the transmitted pulse within a time window, e.g., 100 $\mu$sec. The time window may begin immediately or shortly after the transmitted pulse has been transmitted. In determining the time of detection of the transmitted pulse by each receiving transducer, the distance circuitry 60 interprets the first signal that the threshold detector 58 detects within the time window as the received pulse.

With regard to the imaging transducer 22, the distance circuitry 60 will listen for the receive pulse during the dead period immediately after receiving the trigger signal from the image control/processing circuitry 24. Assuming that the imaging assembly 38 rotates at a rate of 30 revolutions per second, and the pulse generator 46 generates 256 pulses per revolution, the imaging transducer 22 will transmit ultrasound pulses at a rate of 7 to 8 pulses per millisecond. Thus, multiple pulses will be received from the imaging transducer 22 within the 1 millisecond dead period. Once the first trigger signal from the imaging/processing circuitry 24 has been received during the dead period, the distance circuitry 60 will take the first pulse received by the receiving transducers.

To prevent or minimize ultrasound interference that may otherwise result from the transmission of ultrasound energy from the imaging transducer 22 during the imaging function, the ranging circuitry 26 preferably includes filtering circuitry. For example, the emission of ultrasound energy from the imaging transducer 22 may cause the measured distance between a transmitting transducer and a receiving transducer to be less than it actually is. To minimize this adverse effect, multiple distance measurements between each combination of transducers can be taken for each measurement cycle. The greatest distance measurement can then be selected from the multiple distance measurements to obtain the true measurement between the transducers. Such a filtering technique is disclosed in U.S. patent application Ser. No. 10/213,441, entitled "Performing Ultrasound Ranging in the Presence of Ultrasound Interference," which is fully and expressly incorporated herein by reference.

Referring back to FIG. 1, the guidance subsystem 14 further comprises a graphical processor 28 for using the ranging information contained in the distance matrix generated by the ranging circuitry 26 to determine the positions of the tracking transducers 30 within a three-dimensional coordinate system (as established by the reference transducers 32), and graphically rendering the distal end of the catheter body 34, the rotational plane 54 of the imaging assembly 38, and the imaging environment within the three-dimensional coordinate system. The graphical processor 28 may also graphically generate an imaging pattern formed by the rotating imaging element 22, e.g., a conical pattern, and render it within the coordinate system. This technique is detailed in copending U.S. patent application Ser. No. 10/318,474, entitled "Computer Generated Representation of an Imaging Device," which is fully and expressly incorporated herein by reference.

The three-dimensional coordinate system is established by triangulating the relative distance calculations between each reference transducer 32 and the remaining reference transducers 32. That is, the graphical processor 28 utilizes the first eight receive columns and the first eight transmission rows in the distance matrix (d1–d7, d13–d19, d25–d31, d37–d43, d49–d55, d61–d67, d73–d79, and d85–d91) illustrated in FIG. 7. As previously described, placement of the reference transducers 32 in three-dimensional space (at least three transducers defining a plane, and at least one transducer located off of the plane) is sufficient to establish the three-dimensional coordinate system. The coordinates of the tracking transducers 30 within this three-dimensional coordinate system are determined by triangulating the relative distance calculations between each of the tracking transducers 30 and the reference transducers 32. That is, the graphical processor 28 utilizes the last five receive columns and the first eight transmission rows in the distance matrix (d8–d12, d20–d24, d32–d36, d44–d48, d56–d60, d68–d72, d80–d84, and d92–d96) illustrated in FIG. 7. The coordinates of the imaging transducer 22 within the three-dimensional coordinate system are likewise determined by triangulating the relative distance calculation between the imaging transducer 22 and the reference transducers 32. To simplify the processing, this is accomplished by treating the imaging transducer 22 as one of the tracking transducers 30 (i.e., assuming that it is a receiving transducer) and treating the reference transducers 32 as transmitting transducers. This can be performed by transposing a portion of the ninth transmission row of the distance matrix (d97–d104) onto an additional receive column, as illustrated in FIG. 7.

Once the positional coordinates of the tracking transducers 30 and imaging transducer 22 have been determined, the graphical processor 28 can determine the positional coordinates and orientation of the distal ends of the imaging catheter 20 and mapping catheter. Specifically, the graphical processor 28 can determine this information by extrapolating the determined positions of the tracking transducers 30 and imaging transducer 22 based on the known structure of the imaging catheter body 34 and mapping catheter and the positional relationship between these transducers. In the preferred embodiment of the imaging catheter 20, the portion of the distal end between the imaging transducer 22 and the adjacent tracking transducer 30 is relatively stiff, and thus, there will typically be no or very little curve in that portion to extrapolate. Rather, the imaging catheter 20 will tend to bend between that adjacent tracking transducer 30 and the proximal-most tracking transducer 30. As such, the "creep" of the imaging transducer 30 will have little or no adverse effect on the calculation of the positional coordinates and orientation of the imaging catheter 20.

The positional coordinates of the origin of rotational plane 54 can be determined from the positional coordinates of the imaging transducer 22, and the orientation of the rotational plane 54 can be determined from the extrapolated orientation of the portion of the catheter body 34 that contains the imaging transducer 22. The graphical processor 28 is optionally configured to reconstruct the body cavity in which the image is generated by determining the positional coordinates of a roving tracking transducer (e.g., one of the tracking transducers 30 located on the mapping catheters) that is placed in contact with the inner surface of the body cavity. Additional details on determining the location and orientation of ultrasound transducers and the catheters that carry them, as well as body cavity reconstruction techniques, can be found in U.S. patent application Ser. No. 08/905,090, entitled "System for Electrode Localization Using Ultrasound," and U.S. patent application Ser. No. 09/128,304, entitled "A dynamically alterable three-dimensional graphical model of a body region," which are fully and expressly incorporated herein by reference.

Referring still to FIG. 1, the composite image generator 16 is configured for superimposing the image data obtained from the image control/processing circuitry 24 over the three-dimensional information obtained from the graphical processor 28 using known mathematical techniques, and displaying the composite image data on the display 18. Significantly, the origin and orientation of the image data can be obtained from the positional coordinates and orientation of the rotational plane 54.

In the foregoing specification, the invention has been described with reference to a specific embodiment thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, and the invention can be performed using different or additional process actions, or a different combination or ordering of process actions. As another example, features known to those of skill in the art can be added to the embodiment. Other processing steps known to those of ordinary skill in the art may similarly be incorporated as desired. Additionally and obviously, features may be added or subtracted as desired. Accordingly, the invention is not to be restricted except in light of the attached claims and their equivalents.

What is claimed is:

1. A method of localizing an ultrasound imaging transducer, comprising:
   operating the ultrasound imaging transducer in a first resonant mode to transmit an ultrasound imaging signal;
   generating image data based on the transmitted ultrasound imaging signal;
   operating the ultrasound imaging transducer in a second resonant mode to transmit or receive an ultrasound positioning signal, the second resonant mode being different from the first resonant mode; and
   determining a position of the imaging transducer based on the transmitted or received ultrasound positioning signal.

2. The method of claim 1, wherein the imaging signal is transmitted into the body of a patient, and the image data is tissue image data.

3. The method of claim 2, further comprising introducing the imaging transducer within the body of the patient.

4. The method of claim 1, wherein the image data generation comprises processing a reflected portion of the transmitted imaging signal.

5. The method of claim 1, wherein the imaging transducer position determination comprises calculating a distance between the imaging transducer and one or more ultrasound reference transducers by calculating a time period defined by the time of flight of the positioning signal between the imaging transducer and the one or more reference transducers.

6. The method of claim 1, wherein the position of the imaging transducer is determined within a three-dimensional coordinate system.

7. The method of claim 1, further comprising rotating the imaging transducer around an axis, wherein the image data comprises 360° cross-sectional image data.

8. The method of claim 1, wherein the imaging signal and positioning signal comprise ultrasound pulses.

9. The method of claim 1, wherein the imaging transducer is operating in the first and second resonant modes by stimulating the imaging transducer with a single electrical signal.

10. The method of claim 1, wherein the imaging and positioning signals are 9 and 1 MHz signals, respectively.

11. The method of claim 1, wherein the imaging transducer is disk-shaped, the first resonant mode is a thickness mode, and the second resonant mode is a radial mode.

12. The method of claim 1, wherein the imaging transducer exhibits a first isotropy ratio when operated in the first resonant mode, and a second isotropy ratio greater than the first isotropy ratio when operated in the second resonant mode.

13. The method of claim 12, wherein the second isotropy ratio is less than 10.

14. The method of claim 12, wherein the second isotropy ratio is equal to or less than 6.

15. The method of claim 1, wherein the imaging transducer is operated in the second mode to transmit the positioning signal.

16. The method of claim 1, wherein the imaging transducer is operated in the second mode to receive the positioning signal.

17. An ultrasound imaging transducer localization system, comprising:

an ultrasound imaging transducer having first and second resonant modes; and control/processing circuitry coupled to the imaging transducer for operating the imaging transducer in the first resonant mode to transmit an ultrasound imaging signal, and for operating the imaging transducer in the second resonant mode to transmit or receive an ultrasound positioning signal, the control/processing circuitry configured for generating image data based on the transmitted imaging signal, and for determining a position of the imaging transducer based on the transmitted or received positioning signal.

18. The system of claim 17, further comprising a probe, wherein the imaging transducer is mounted on the probe.

19. The system of claim 18, wherein the probe is a catheter.

20. The system of claim 17, wherein the imaging transducer is rotatable.

21. The system of claim 17, wherein the control/processing circuitry generates the image data by processing a reflected portion of the transmitted imaging signal.

22. The system of claim 17, wherein the control/processing circuitry is configured for determining the position of the imaging transducer by calculating a distance between the imaging transducer and one or more ultrasound reference transducers by calculating a time period defined by the time of flight of the positioning signal between the imaging transducer and the one or more reference transducers.

23. The system of claim 17, wherein the control/processing circuitry is configured for determining the position of the imaging transducer within a three-dimensional coordinate system.

24. The system of claim 17, further comprising a drive unit mechanically coupled to the imaging transducer for rotating the imaging transducer around an axis, wherein the one or more processors are configured for generating 360° cross-sectional image data.

25. The system of claim 17, wherein the imaging signal and positioning signal comprise ultrasound pulses.

26. The method of claim 17, wherein the control/processing circuitry is configured for operating the imaging transducer in first and second resonant modes by stimulating the imaging transducer with a single electrical signal.

27. The system of claim 17, wherein the imaging and positioning signals are 9 and 1 MHz, respectively.

28. The system of claim 17, wherein the imaging transducer is disk-shaped, the first resonant mode is a thickness mode, and the second resonant mode is a radial mode.

29. The system of claim 17, wherein the imaging transducer exhibits a first isotropy ratio when operated in the first resonant mode, and a second isotropy ratio greater than the first isotropy ratio when operated in the second resonant mode.

30. The system of claim 29, wherein the second isotropy ratio is less than 10.

31. The system of claim 29, wherein the second isotropy ratio is equal to or less than 6.

32. The system of claim 17, wherein the control/processing circuitry is configured for operating the imaging transducer in the second mode to transmit the positioning signal.

33. The system of claim 17, wherein the control/processing circuitry is configured for operating the imaging transducer in the second mode to transmit the positioning signal.

* * * * *

UNITED STATES PATENT AND TRADEMARK OFFICE
CERTIFICATE OF CORRECTION

PATENT NO.    : 6,719,700 B1
DATED         : April 13, 2004
INVENTOR(S)   : N. Parker Willis It is certified that error appears in the above-identified patent and that said Letters Patent is hereby corrected as shown below:

Column 2,
Line 33, remove "." between words "an ultrasound"

Column 5,
Line 51, remove "." between word "patent application"

Signed and Sealed this

Sixth Day of July, 2004

JON W. DUDAS
*Acting Director of the United States Patent and Trademark Office*